US011376385B2

(12) United States Patent
Klee et al.

(10) Patent No.: US 11,376,385 B2
(45) Date of Patent: Jul. 5, 2022

(54) MASK WEAR-OUT ASSESSMENT SYSTEM

(71) Applicant: KONINKLIJKE PHILIPS N.V., Eindhoven (NL)

(72) Inventors: Mareike Klee, Straelen (DE); Nocolaas Petrus Willard, Valkenswaard (NL); Joyce Van Zanten, Waalre (NL); Lutz Christian Gerhardt, Eindhoven (NL); Jacob Roger Haartsen, Eindhoven (NL); Cornelis Bernardus Aloysius Wouters, Echt (NL); Jan Henrik Poesse, Eindhoven (NL)

(73) Assignee: Koninklljke Philips N.V., Eindhoven (NL)

( * ) Notice: Subject to any disclaimer, the term of this patent is extended or adjusted under 35 U.S.C. 154(b) by 1745 days.

(21) Appl. No.: 15/105,675

(22) PCT Filed: Dec. 15, 2014

(86) PCT No.: PCT/EP2014/077795
§ 371 (c)(1),
(2) Date: Jun. 17, 2016

(87) PCT Pub. No.: WO2015/091376
PCT Pub. Date: Jun. 25, 2015

(65) Prior Publication Data
US 2016/0321420 A1 Nov. 3, 2016

(51) Int. Cl.
*A61M 16/06* (2006.01)
*G16H 40/40* (2018.01)
(Continued)

(52) U.S. Cl.
CPC ........ *A61M 16/0616* (2014.02); *A61M 16/06* (2013.01); *A61M 16/0683* (2013.01);
(Continued)

(58) Field of Classification Search
CPC ......... H04W 84/12; A61M 2016/0015; A61M 2016/0027; A61M 2016/003;
(Continued)

(56) References Cited

U.S. PATENT DOCUMENTS 6,240,921 B1 * 6/2001 Brydon ............. A61M 16/0051
128/204.18
8,228,187 B2 * 7/2012 Yu ........................ A61B 5/0008
128/204.23
(Continued)

FOREIGN PATENT DOCUMENTS

CN 101516300 A 8/2009
CN 102427840 A 4/2012
(Continued)

OTHER PUBLICATIONS

In re Beauregard, 53 F.3d 1583 (Fed. Cir. 1995). (Year: 1995).*
(Continued)

*Primary Examiner* — Timothy A Stanis
*Assistant Examiner* — Benjamin M. Kusiak
(74) *Attorney, Agent, or Firm* — Michael W. Haas

(57) ABSTRACT

The present disclosure relates to a wear-out assessment system including a patient interface for delivering a flow of breathable gas to an airway of a patient, wherein the patient interface includes a first wireless communication unit a communication device including a second wireless communication unit configured to wirelessly communicate with the first wireless communication unit and a wear-out assessment unit for determining wear-out data relating to a wear-out of the patient interface. The first and second wireless communication unit are configured to exchange at least parts of the wear-out data. The present disclosure also relates to a method of assessing wear-out of a patient interface.

10 Claims, 11 Drawing Sheets

(51) Int. Cl.
*H04W 4/80* (2018.01)
*A61M 15/00* (2006.01)
*A61M 16/00* (2006.01)
*H04W 84/12* (2009.01)

(52) U.S. Cl.
CPC .............. *G16H 40/40* (2018.01); *H04W 4/80* (2018.02); *A61M 15/008* (2014.02); *A61M 15/0083* (2014.02); *A61M 2016/0027* (2013.01); *A61M 2205/13* (2013.01); *A61M 2205/18* (2013.01); *A61M 2205/332* (2013.01); *A61M 2205/3306* (2013.01); *A61M 2205/3331* (2013.01); *A61M 2205/3368* (2013.01); *A61M 2205/3553* (2013.01); *A61M 2205/3569* (2013.01); *A61M 2205/3592* (2013.01); *A61M 2205/50* (2013.01); *A61M 2205/581* (2013.01); *A61M 2205/584* (2013.01); *A61M 2205/70* (2013.01); *A61M 2230/63* (2013.01); *H04W 84/12* (2013.01)

(58) Field of Classification Search
CPC ............ A61M 16/0051; A61M 16/022; A61M 16/024; A61M 16/0027; A61M 2209/01; A61M 2230/50; A61M 2230/63; A61M 2230/65; A61M 15/008; A61M 15/0085; A61M 2205/13; A61M 2205/18; A61M 2205/3507; A61M 2205/3546; A61M 2205/3553; A61M 2205/3561; A61M 2205/3569; A61M 2205/3576; A61M 2205/3584; A61M 2205/3592; A61M 2205/50; A61M 2205/52; A61M 2205/581; A61M 2205/584; A61M 2205/70; A61M 2205/6009; A61M 2205/3306; A61M 2205/332; A61M 2205/3331; A61M 2205/3368
USPC ............. 128/204.21, 204.23, 204.18, 205.23
See application file for complete search history.

(56) References Cited

U.S. PATENT DOCUMENTS

| 8,545,416 | B1* | 10/2013 | Kayyali | A61B 5/085 |
| | | | | 128/204.23 |
| 8,616,203 | B2 | 12/2013 | Jaffe | |
| 9,202,008 | B1* | 12/2015 | Frederick | G16H 40/20 |
| 9,301,878 | B2 | 4/2016 | Raksi | |
| 9,533,114 | B1* | 1/2017 | Kayyali | A61B 5/085 |
| 2005/0188991 | A1* | 9/2005 | Sun | A61B 5/0002 |
| | | | | 128/204.23 |
| 2007/0095350 | A1* | 5/2007 | Darkin | A61M 16/0825 |
| | | | | 128/206.24 |
| 2009/0071478 | A1* | 3/2009 | Kalfon | A61M 16/0858 |
| | | | | 128/204.17 |
| 2009/0199857 | A1* | 8/2009 | Peake | A61M 16/06 |
| | | | | 128/206.28 |
| 2009/0241962 | A1* | 10/2009 | Jafari | A61M 16/026 |
| | | | | 128/205.25 |
| 2010/0078017 | A1* | 4/2010 | Andrieux | H04B 7/2606 |
| | | | | 128/202.22 |
| 2011/0043357 | A1* | 2/2011 | Peatfield | A61M 5/1413 |
| | | | | 340/522 |
| 2011/0132370 | A1* | 6/2011 | Farrugia | A61B 5/14532 |
| | | | | 128/204.23 |
| 2011/0247620 | A1* | 10/2011 | Armstrong | A61M 16/0677 |
| | | | | 128/204.23 |
| 2012/0040612 | A1 | 2/2012 | Lee et al. | |
| 2012/0065588 | A1 | 3/2012 | Cirillo | |
| 2012/0137250 | A1* | 5/2012 | Milne | A61M 16/0063 |
| | | | | 715/808 |
| 2012/0240927 | A1* | 9/2012 | Bathe | A61M 16/20 |
| | | | | 128/203.12 |
| 2013/0139824 | A1 | 6/2013 | Mazzone | |
| 2013/0263857 | A1 | 10/2013 | Ahmad | |
| 2014/0020684 | A1* | 1/2014 | Klasek | A61M 16/16 |
| | | | | 128/203.26 |
| 2015/0238716 | A1* | 8/2015 | Budhiraja | A61M 16/0633 |
| | | | | 128/203.14 |
| 2015/0250972 | A1* | 9/2015 | Haibach | A61M 16/0816 |
| | | | | 128/202.27 |
| 2015/0367092 | A1* | 12/2015 | Goff | A61M 16/0057 |
| | | | | 128/204.23 |
| 2016/0193437 | A1* | 7/2016 | Bao | G16H 40/63 |
| | | | | 128/203.14 |

FOREIGN PATENT DOCUMENTS

| CN | 103037754 A | 4/2013 |
| EP | 0661071 A1 | 7/1995 |
| GB | 2443654 | 5/2008 |
| JP | 2006085344 | 3/2006 |
| JP | 2010058427 | 3/2010 |
| RU | 2392010 | 6/2010 |
| SU | 702559 | 2/1984 |
| WO | WO02078775 A2 | 10/2002 |
| WO | WO2007098540 A1 | 9/2007 |

OTHER PUBLICATIONS

"Orange Business Services and Weinmann develop homecareONLINE, an end-to-end telemedicine solution for sleep apnea patients", press release, Paris and Hamburg, Germany, Sep. 5, 2013 http://www.orange.com/en/press/press-releases/press-releases-2013/Orange-Business-Services-and-Weinmann-develop-homecareONLINE-an-end-to-end-telemedicine-solution-for-sleep-apnea-patients.

Sarasohn-Kahn, J., "Making Sense of Sensors—How New Technologies Can Change Patient Care", California HelathCare Foundation, pp. 1-21, Feb. 2013 http://www.chcf.org/~/media/MEDIA%20LIBRARY%20Files/PDF/M/PDF%20MakingSenseSensors.pdf.

"The International Educational and Networking Forum for eHealth, Telemedicine and Health ICT", Med-e-Tel Newsletter, Mar. 28, 2008 http://archive.constantcontact.com/fs073/1101836993790/archive/1102035580741.html.

Perez, S. "The "Zizz" is an Intelligent Sleep Mask That Helps You Get Better Zzz's", Saturday, Sep. 14, 2013 http://techcrunch.com/2013/09/14/the-zizz-is-an-intelligent-sleep-mask-which-helps-you-get-better-zzzs/.

* cited by examiner

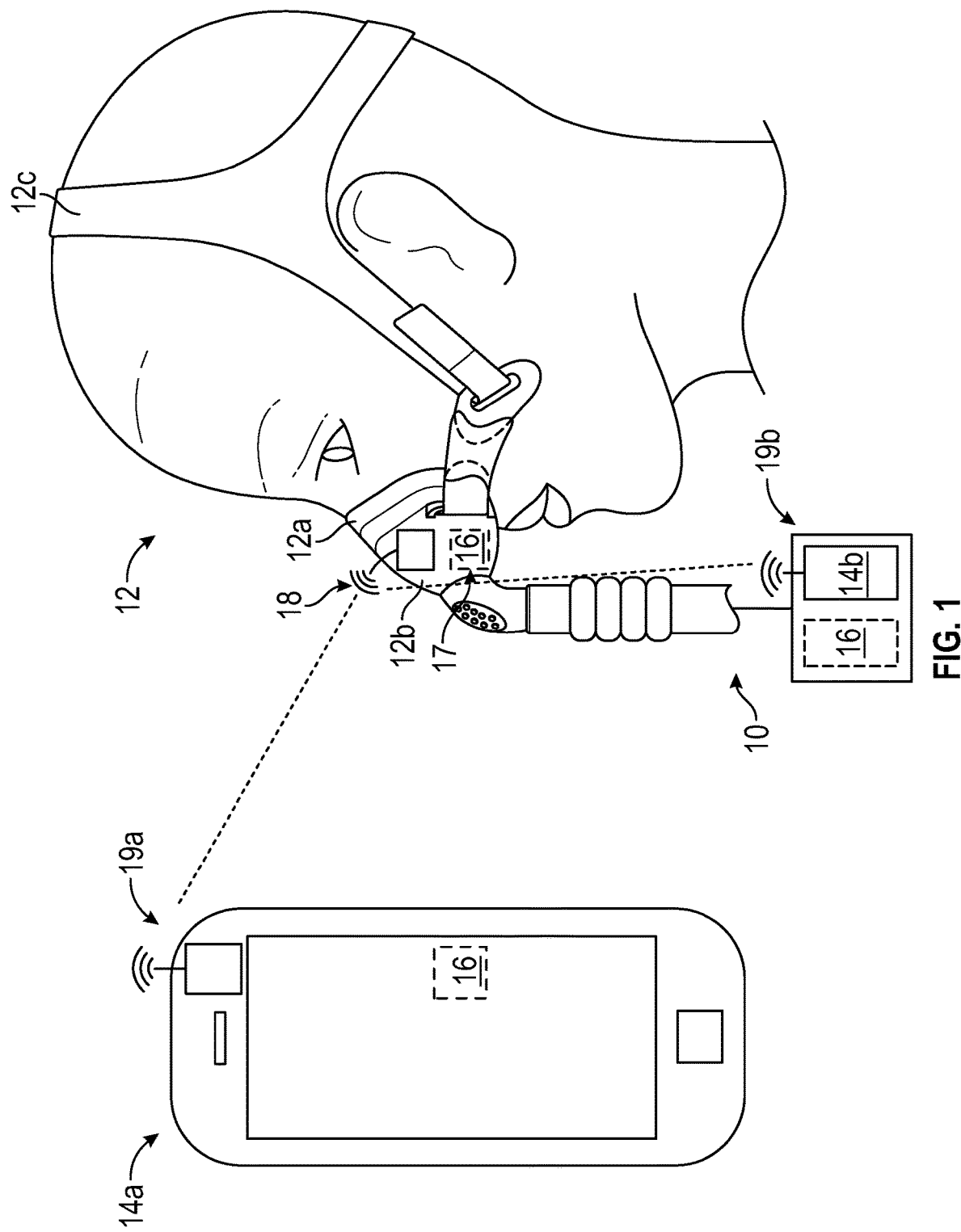

MASK WEAR-OUT ASSESSMENT SYSTEM

CROSS-REFERENCE TO RELATED APPLICATIONS

This patent application claims the priority benefit under 35 U.S.C. § 371 of international patent application no. PCT/EP2014/077795, filed Dec. 15, 2014, which claims the benefit of European Patent Application No. EP13198909.7, filed on Dec. 20, 2013, which is hereby incorporated by reference herein.

FIELD OF THE INVENTION

The present invention relates to a wear-out assessment system that is able to determine various forms of wear-out of a patient interface that is used for delivering a gas to a user. Such gases like air, cleaned air, oxygen, or any modification thereof are submitted to the user (also referred to as a patient) via the patient interface in a pressurized or unpressurized way. Further, the invention relates to a respective patient interface for delivering a flow of breathable gas to an airway of a patient and to a method for assessing the wear-out of the patient interface. Additionally, the present invention relates to a computer program for carrying out the method.

BACKGROUND OF THE INVENTION

For several breathing-related illnesses or diseases the usage of such a patient interface is necessary or at least advisable. One non-limiting example of such a disease is Obstructive Sleep Apnea or Obstructive Sleep Apnea Syndrome (OSA). Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway of the patient in order to keep it open. Various mask types can be used to apply the positive airway pressure to the patient.

Examples for patient interfaces are:

nasal masks, which fit over the nose and deliver gas through the nasal passages, oral masks, which fit over the mouth and deliver gas through the mouth, full face masks, which fit over both, the nose and the mouth, and deliver gas to both, and nasal pillows, which are regarded as masks as well within the scope of the present invention and which consist of small nasal inserts that deliver the gas directly to the nasal passages.

Such a mask forms a seal around a nose and/or mouth of a patient's face, providing an interface between the air source and the patient's respiratory system that is ideally free of leaks. During the treatment, the patient wearing the mask inhales the pressurized air, which prevents tongue tissue from obstructing the air passages. Because of the use of pressurized air, the facial mask ideally provides an airtight seal between the mask and the patient's face.

A mask typically comprises a soft cushion that is used as mask-to-patient interface, i.e. that contacts the face of the patient when the mask is worn, and it comprises a so-called mask shell building a rigid or semi-rigid holding structure for holding the cushion in place and for supplying mechanical stability to the patient interface. The rigid shell typically comprises polycarbonate and the cushion (also denoted as mask sealing flap) typically comprises silicone. Additionally, the mask may be fixed to the patient's face by means of a headgear. However, the various materials of the mask may degrade over time, thereby leading to impaired mask material properties. For example, the silicone of the mask sealing flap, which is in contact with the patient's face, can exhibit discoloration or growing biofilm on the flap surface when in contact with the patient's skin for a long period of time. This biofilm can degrade the silicone over time, at least if it is not washed away on a regular basis. Similarly, the headgear made out of textile shows changes of its mechanical properties due to the continuous usage of the mask. As a result of the described mask aging, it is normally advised to exchange parts of the masks regularly, preferably every three to six months.

Although there is a possibility for sleep apnea patients to exchange their mask or parts of the patient interface every three to six months, only few patients make use of this option. Many patients just forget to regularly organize a new mask. Instead, they sometimes use their old masks for several years, wherein biofilms are grown on the mask sealing flap or other parts of a mask (e.g. headgear), especially if the masks are not cleaned regularly. These biofilms can lead to skin irritations and/or skin infections, inflammation or other bacteria-induced infections such as pulmonary infections or infections of the respiratory system through biofilms present on mask materials and entering the respiratory system during use of CPAP. Moreover, the biofilms can degrade the silicone properties and can affect the sealing capabilities of the sealing flap. This in turn may cause the mask to leak when pressure is applied during the CPAP treatment. A degraded mask reduces patient tolerance and compliance with the applied medical procedure.

US 2009/0199857 A1 describes a reminder system for a patient to service and/or replace a CPAP mask or a component thereof. However, the provided reminder system only shows a limited usability.

US 2013/0263857 A1 relates to a respiratory assistance device that is in communication with a mask and that indicates a fit status of said mask. Upon initiating a therapeutic gas delivery from the respiratory assistance device to the mask, one or more measurements from respective one or more sensors of the respiratory assistance device are received. A leakage value from these measurements is derived, and a mask fit index is assigned.

EP 0 661 071 A1 relates to a device for continuous positive airway pressure breathing (CPAP).

SUMMARY OF THE INVENTION

Accordingly, it is an object of the present invention to provide a wear-out assessment system, a respective patient interface, a method and computer program product that overcome the above-described shortcomings.

In a first aspect of the present invention, a wear-out assessment system is presented that comprises:

a patient interface for delivering a flow of breathable gas to an airway of a patient, wherein the patient interface comprises a first wireless communication unit, a communication device comprising a second wireless communication unit configured to wirelessly communicate with the first wireless communication unit, and a wear-out assessment unit for determining wear-out data relating to a wear-out of the patient interface, wherein the first and second wireless communication unit are configured to exchange at least parts of the wear-out data.

In a further aspect of the present invention, a patient interface for delivering a flow of breathable gas to an airway of a patient is presented that comprises:

a wireless communication unit for wirelessly communicating with a communication device, and a wear-out assessment module for determining wear-out data relating to a wear-out of the patient interface and to exchange at least parts of the wear-out data via the wireless communication unit with the communication device.

In a further aspect of the present invention, a method for assessing the wear-out of a patient interface configured to deliver a flow of breathable gas to an airway of a patient is presented. The method comprises:

determining wear-out data relating to the wear-out of the patient interface, exchanging at least parts of the wear-out data between the patient interface and a communication device by means of a wireless communication, and issuing on the communication device, depending on the wear-out data, a reminder to the patient to service and/or replace at least parts of the patient interface.

In an even further aspect of the present invention, a computer program product is presented that comprises code for causing a processor, when the code is executed on the processor, to enable the wear-out assessment system to execute the disclosed method.

Preferred embodiments of the invention are defined in the dependent claims. It shall be understood that the claimed patient interface, the claimed method and the claimed computer program product have similar and/or identical preferred embodiments as the claimed wear-out assessment system and as claimed in the dependent claims.

The present invention, inter alia, relates to a wear-out assessment system for detecting a wear-out of a patient interface. The system allows determining wear-out data of the patient interface, which wear-out data may then be transferred from the patient interface to an external communication device. The wear-out assessment unit that determines these wear-out data may be part of the patient interface, part of the communication device and/or part of an external computer system.

In an embodiment, the wear-out assessment unit may be configured to determine and acquire quantitative measurement parameters (e.g. air flow, leakage, pressure, skin or gas temperature, material color, material stiffness/hardness) related to the performance or wear-out of the patient interface. These measurement parameters may form a part of the wear out data.

According to an embodiment, the wear-out assessment unit may be configured to issue on the communication device, depending on the wear-out data, a reminder to the patient to service and/or replace at least parts of the patient interface. The reminder may comprise a request to clean the patient interface and/or a query whether a new patient interface or parts thereof should be ordered, for example, from a mask distributor. Thereby, the patient is prevented from using an old and contaminated patient interface. A regular service or replacement of the patient interface keeps the patient interface in a proper and operative condition. As a consequence, possible problems arising from material changes or degradation such as air leakages and skin irritations/infections can be avoided. The compliance to the therapy can also be enhanced due to the high wearing comfort of the patient interface. By automatically exchanging the wear-out data between the first and the second wireless communication unit and by automatically presenting the reminder on the communication device based on the exchanged wear-out data, a very user friendly wear-out assessment is provided. So, the reminder to service and/or replace at least parts of the patient interface can be received by the patient, even if the patient is not in visual contact with the patient interface. The exchange of the wear-out data between the first and the second wireless communication unit may be a one-time event or may be performed on a regular basis.

It shall be noted that the above-mentioned first and second wireless communication units shall not only denote active, but also passive communication units.

In an embodiment, the wear-out assessment unit comprises a timer for measuring a usage time of the patient interface and/or a counter for measuring a usage count of the patient interface, wherein the wear-out assessment unit is configured to determine the wear-out data based on the usage time and/or usage count.

The timer may be started when the patient receives the patient interface and starts using it. In particular, the timer may monitor the total time after the patient has received the patient interface (i.e. the product lifetime, regardless whether the patient interface is actually used or not) and/or may monitor the time periods, when the patient interface is actually used during a therapy session. Alternatively or additionally, the wear-out assessment unit comprises a counter that is increased each time the patient uses the patient interface for a therapy session.

In a further embodiment, the wear-out assessment unit is configured to trigger the timer and/or to increase the counter if an approach between the patient interface and the communication device is detected by means of the first and/or second wireless communication unit.

In this embodiment, the first and/or second wireless communication unit are able to detect that a distance between the patient interface and the communication device falls below a predetermined distance. As soon as such an approach is detected, a wireless communication between the first and the second wireless communication unit is triggered. On the basis of this wireless communication, the timer is started (again) and/or the counter is increased. In one exemplary embodiment, a timer measuring the total time can also be combined with a counter counting the number of usages of the patient interface. This allows a more precise determination of the wear-out of the patient interface, since the actual usage of the patient interface is taken into account. In this context, it is assumed that an approach between the patient interface and the communication device is an indicator for an upcoming therapy session.

In another embodiment, the wear-out assessment unit comprises a sensor for detecting a usage of the patient interface, wherein the wear-out assessment unit is configured to trigger the timer and/or to increase the counter if the usage of the patient interface is detected.

By means of the sensor the duration of a therapy session as well as the number of therapy sessions/usages can be measured. Thereby, the wear-out of the patient interface can be exactly determined. Moreover, the sensor allows an automatic detection of a patient interface usage. As a result, the usage of the patient interface is reliably taken into account for the determination of the wear-out. A situation where the patient uses the patient interface for a therapy session, but forgets to "register" the mask usage can be avoided. Due to the sensor, it is possible to couple the issuance of the reminder to a really measured wear-out level.

It is not always necessary to replace the mask after a fixed time interval, if the mask has not been worn that often, for example. This may lead to improved cost efficiency.

In a further embodiment, the sensor comprises a motion sensor for measuring a movement of the patient interface or sleep related body movements of the patient. The motion sensor may be configured to detect a general movement of the patient interface, but may also be configured to detect a specific movement pattern that is related to the pressure therapy. The motion sensor may thus be used to trigger the timer and/or the counter. By way of example, the motion sensor may comprise an acceleration sensor.

In another embodiment, the sensor comprises a contact sensor for detecting a contact between the patient interface and a patient's face. The contact sensor can be configured to detect an electric conductivity of the skin of the patient's face. Thus, the usage of the patient interface can be reliably detected. As a consequence, the wear-out of the patient interface can be determined more precisely.

According to another embodiment, the sensor comprises a pressure sensor, e.g. for sensing a contact pressure between the patient interface and the face of the patient.

According to another embodiment, the sensor comprises a temperature sensor for measuring a temperature of the patient's face. As soon as the patient interface is in contact with the patient's face, the temperature sensor detects a temperature in a range that is characteristic for a human body temperature or skin surface temperature in different ambient conditions (e.g. 20-50° C.). The temperature sensor would then trigger the timer and/or the counter. Therefore, the usage of the patient interface can be detected and the wear-out data can be determined.

According to another embodiment, the sensor comprises a humidity sensor for measuring an amount of moisture in the sealed area between the patient's face and the patient interface. As soon as the patient interface is in contact with the patient's face, the humidity sensor detects a bigger amount of moisture and would then trigger the timer and/or the counter. Therefore, the usage of the patient interface can be detected and the wear-out data can be determined.

According to another embodiment, the sensor comprises an elongation sensor for determining an elongation within a headgear of the patient interface. In particular, the elongation sensor can be arranged in the headgear straps and can be configured to detect changes of the material properties of the headgear. Thereby, for example, elongation changes in a textile used in the headgear straps can be detected. Based on the elongation changes, the wear-out data may be determined.

In another embodiment, the wear-out assessment unit comprises a camera for capturing an image of the patient interface, wherein the wear-out assessment unit is configured to determine the wear-out data based on the characteristics of the captured image.

For example, if a strong biofilm is grown on the mask sealing flap, the color and/or transparency of the mask sealing flap may change, i.e. the sealing flap may become more opaque or yellow. Therefore, by analyzing the color and/or transparency of the captured image, it is possible to determine the wear-out of the patient interface. Consequently, the wear-out of the patient interface can be precisely determined.

In a further embodiment, the first and second wireless communication unit are configured to wirelessly communicate with each other by means of near field communication (NFC) and/or Bluetooth technologies.

These proximity based communication technologies allow starting the communication as soon as the approach distance between the patient interface and the communication device falls below a predetermined threshold. As the wireless communication is started automatically, the wear-out assessment system provides a very easy handling. For exchanging the wear-out data it is not necessary, for example, to manually provide contact data of the peer entity (e.g. the patient interface/communication device) to trigger the wireless communication. It is sufficient that the patient interface and the communication device approach each other. For example, the information exchange can be done via NFC. As a further option, NFC can be used to automatically setup a Bluetooth connection, wherein the information exchange may be done via Bluetooth. Alternatively, also any other wireless communication technologies can be applied, like Wi-Fi.

According to another embodiment, the wear-out assessment unit comprises:

a determining component for determining a wear-out level of the patient interface based on a recorded wear-out of the patient interface, an evaluation component for evaluating the wear-out level and for outputting a wear-out event if the wear-out level exceeds a predetermined wear-out threshold, and a presentation component for issuing a reminder to the patient based on the wear-out-event.

Some of these components may be arranged on the patient interface, while the other components are arranged on the communication device. It is even possible to split one single component to reside on the patient interface as well as on the communication device. Further, at least some of the components can also be implemented on a computer system that is located, for example, on the Internet. In general, the components can be realized as hardware and/or software components. This arrangement of the above mentioned components provides a very flexible architecture for the wear-out assessment unit. The first and second wireless communication unit can be configured to exchange the wear-out data between the different components of the wear-out assessment unit. The wear-out data may comprise initial patient interface data (like e.g. type of mask, production code of the mask, characteristics of an initial image of the patient interface after the manufacturing process, expected mask lifetime etc.) stored on a patient interface, the wear-out level and/or a wear-out event.

According to another embodiment, the communication device is a mobile communication device or a therapy device for providing pressurized air to the patient interface. The components (i.e. the determining component, the evaluation component and/or the presentation component) to be arranged on the communication device may be provided on the mobile communication device or the therapy device or on both of them.

The mobile communication device may be a smartphone as owned by many of the patients. Advantageously, the patient is already used to the smartphone and can easily operate the different functionalities of the smartphone. Also, the patient is usually familiar with the operation of the therapy device. As a result, a very high ease of handling is provided by realizing at least parts of the wear-out assessment unit on a smartphone and/or therapy device.

In a further embodiment, at least parts of the wear-out assessment unit are implemented by a program code configured to be executed on a smartphone.

The program code, for example, can be a so-called App that can be downloaded from an App Store located on the Internet. The App matching the specific patient interface may be identified by means of initial patient interface data received from the patient interface via the second wireless communication unit. In this context, the initial patient interface data stored on the patient interface may comprise an identification number that is suitable for identifying the specific patient interface.

In a further embodiment, the therapy device is configured to be activated if an approach between the patient interface and the therapy device is detected by means of the second wireless communication unit.

In other words, an approach between the patient interface and the therapy device unlocks the general operation of the therapy device. The pressurized air can only be delivered after the therapy device has been activated/unlocked. This assures, that the therapy session can only be started if the usage of the patient interface has been "registered" at the therapy device. Thus, it can be avoided that the patient uses the patient interface for a therapy session, but forgets to register the usage of the patient interface such that the timer and/or counter may be triggered. This leads to a more reliable determination of the wear-out data.

In a further embodiment, the therapy device is configured to be started manually. As soon as the therapy device detects that the patient interface is in the vicinity of the therapy device (e.g. via proximity communication/detection), the usage of the patient interface is registered.

In a further embodiment of the patient interface, the wear-out assessment module comprises at least some of the determining component, the evaluation component, and/or the presentation component of the wear-out assessment unit. Further, the wear-out assessment module may comprise a wear-out sensor that is configured to determine the wear-out level/the wear-out data of the patient interface. By determining the wear-out data, a reminder can be issued on the communication device to remind the patient to service (for example to clean the patient interface) and/or to replace at least parts of the patient interface. As a result of a well-serviced patient interface, the patient compliance to the therapy can be enhanced.

As mentioned in the beginning, the present invention also relates to a method for assessing the wear-out of the patient interface and for issuing a corresponding reminder to a communication device. In an embodiment of the method, issuing the reminder comprises:

retrieving initial patient interface data stored on the patient interface, identifying the patient interface by means of the initial patient interface data, prompting the patient whether at least parts of the patient interface should be ordered from a mask distributor, and ordering the parts of the patient interface in response to an order of the patient.

This automated ordering is very comfortable and user friendly for the patient. For example, the automated detection of the mask type assures that only correct parts fitting to the specifically used patient interface are ordered from the mask distributor. The patient has only to confirm the parts that should be ordered. The initial patient interface data may comprise data that assure that the patient interface is genuine and not counterfeit.

BRIEF DESCRIPTION OF THE DRAWINGS

These and other aspects of the invention will be apparent from and elucidated with reference to the embodiment(s) described hereinafter. In the following drawings FIG. 1 shows a first embodiment of the proposed wear-out assessment system and the proposed patient interface;

DETAILED DESCRIPTION OF THE INVENTION

Figure 2A:
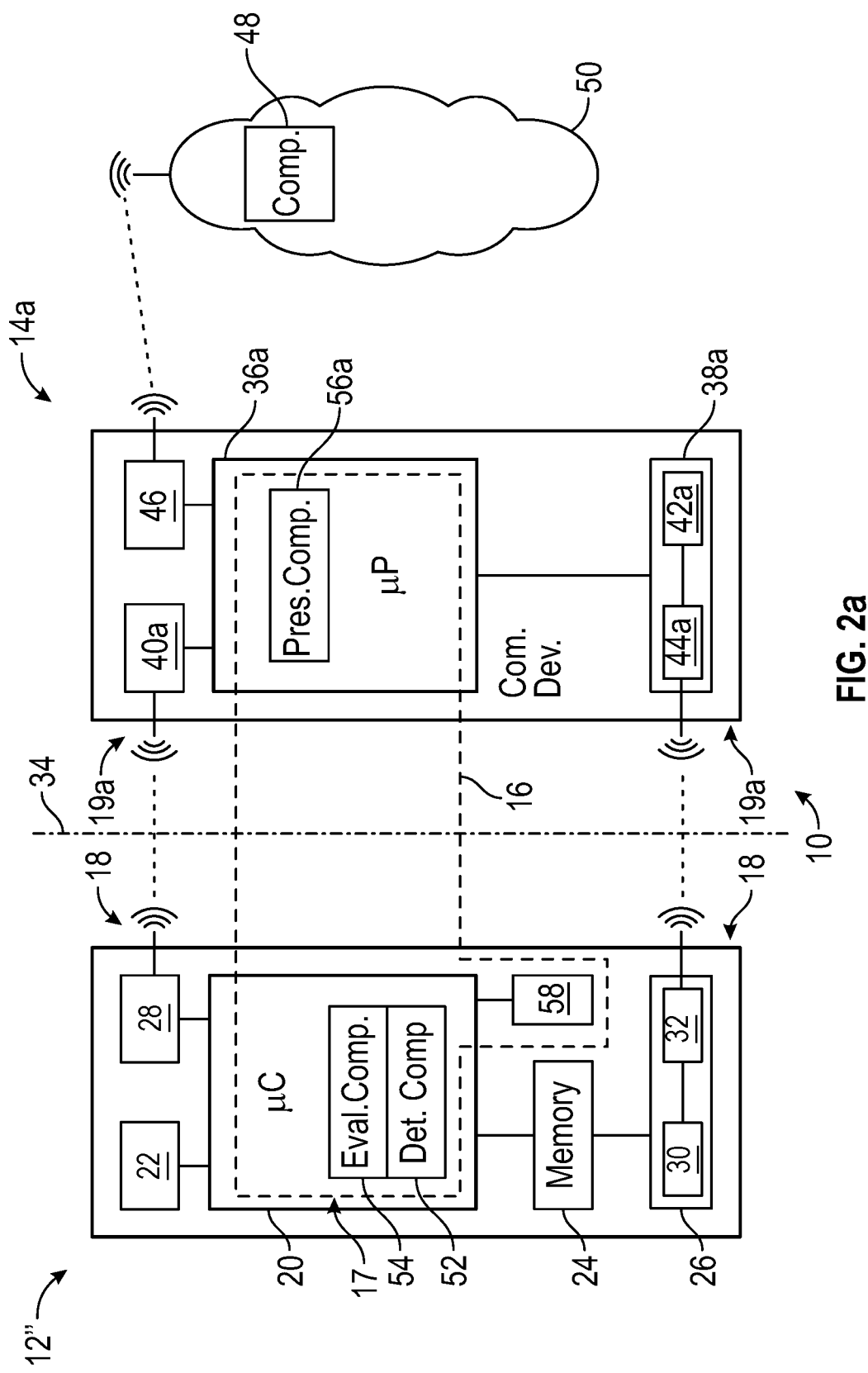
FIG. 2 shows a detailed embodiment of the proposed wear-out assessment system and the proposed patient interface.

FIG. 1 illustrates an embodiment of a wear-out assessment system 10. The wear-out assessment system 10 comprises a patient interface 12 and a communication device. The communication device can be represented by a mobile communication device 14a and/or a therapy device 14b which is configured to provide a pressurized flow of breathable gas to the patient interface 12. By way of example, the mobile communication device 14a can be a smartphone.

In this exemplary embodiment, patient interface device 12 is formed as a nasal mask. However, any type of mask, such as a nasal/oral mask, a nasal pillow/cushion or a full face mask, which facilitates the delivery of the flow of breathable gas to an airway of a patient, may be used while remaining within the scope of the present invention. Patient interface 12 comprises a mask sealing flap 12a coupled to a shell 12b. Mask sealing flap 12a is made of a soft, flexible material, such as, without limitation, silicone, an appropriately soft thermoplastic elastomer, a closed cell foam, or any combination of such materials. In addition, shell 12b is made of a rigid or semi-rigid material such as, without limitation, polycarbonate or silicone. An opening in shell 12b allows the flow of breathable gas from pressure generating therapy device 14b to be communicated to an interior space defined by shell 12b and mask sealing flap 12a, and then to the airway of the patient. Patient interface device 12 also includes a headgear component 12c, which in the illustrated embodiment is a two-point headgear. Headgear component 12c comprises a first and a second strap, each of which is structured to be positioned on the side of the face of the patient above the patient's ear (only the left side strap is shown). It goes without saying that any other options for fixing the patient interface to the patient's face are also within the scope of the present invention.

The mask sealing flap 12a is typically in direct contact with the skin of a patient's face. Thus, the mask sealing flap 12a is likely to be contaminated by a biofilm growing on top of the flap surface. These biofilms can lead to skin irritations and skin infections. Moreover, the aging of the mask sealing flap 12a may lead to air leakages that reduce the efficiency of the therapy.

Further, the straps of the headgear 12c are usually made out of textile and may show changes of the mechanical properties over time due to a continuous usage of the patient interface 12. In particular, the repeated tensioning of the straps of the headgear 12c and skin oils may reduce the elasticity of the straps of the headgear 12c. As a result, the patient interface 12 cannot reliably be secured anymore to the patient's face. Further, air leakages may occur. It is therefore important to service and/or replace at least parts of the patient interface 12 when a certain time period has lapsed. Unfortunately, many of the patients forget this necessary service or replacement.

Due to these reasons, the wear-out assessment system 10 further comprises a wear-out assessment unit 16 for automatically determining wear-out data relating to a wear-out of the patient interface 12. The wear-out assessment unit 16 can either be arranged on the patient interface 12 or on the communication device. Alternatively, parts of the wear-out assessment unit 16 can be realized on the patient interface 12, while the remaining parts are realized on the communication device. As a further option, at least parts of the wear-out assessment unit 16 can be arranged on an external computer system (not shown in FIG. 1). The parts of the wear-out assessment unit 16 that are realized on the patient interface 12 are denominated as wear-out assessment module 17.

The wear-out assessment unit 16 may be configured to determine the wear-out data relating to a wear-out of the mask sealing flap 12a and/or the headgear 12c. At least parts of the wear-out data may be exchanged between the patient interface 12 and the communication device 14. For that purpose, the patient interface 12 may comprise a first wireless communication unit 18, and the communication device may comprise a second wireless communication unit. The first communication unit and the second wireless communication unit may be configured to wirelessly communicate with each other by means of NFC, Bluetooth technologies and/or any other wireless communication technologies and to exchange at least parts of the wear-out data. As an example, the wear-out data may be exchanged via Bluetooth, whereas NFC is used to automatically configure the Bluetooth connection. Depending on these wear-out data, the wear-out assessment unit 16 may be configured to automatically issue a reminder on the communication device in order to remind the patient to service and/or replace the mask sealing flap 12a and/or the headgear 12c or the whole mask.

The reminder to service the mask sealing flap 12a may comprise a request to clean the mask sealing flap 12a for removing potential biofilms. A regular cleaning of the mask sealing flap 12a may lengthen the lifetime of the patient interface 12. In addition, a regular service and/or replacement of the patient interface 12 assure an efficient therapy and thus enhance patient compliance to the therapy.

FIGS. 2 to 5 show detailed embodiments of the wear-out assessment system 10, in particular of the patient interface 12, the communication device and the wear-out assessment unit 16. It shall be understood that the illustrated details of FIGS. 2 to 5 only represent exemplary embodiments and do not restrict the scope of the claims.

Figure 2B:
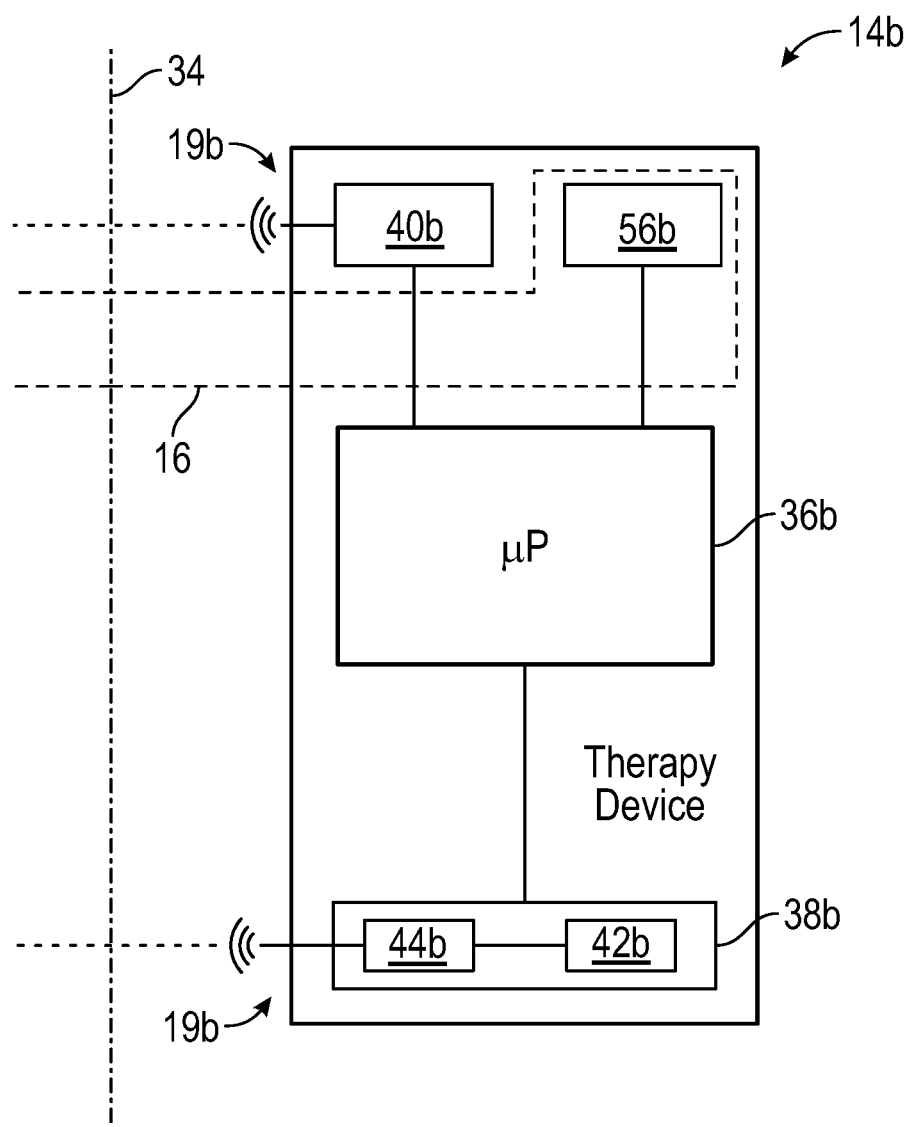

FIGS. 2a and 2b illustrate a first detailed embodiment of the wear-out assessment system 10. The wear-out assessment system 10 comprises the patient interface 12, the smartphone 14a and the therapy device 14b (illustrated in FIG. 2b).

The patient interface 12 may also comprise a microcontroller 20 and a flash memory 22 for storing a firmware that is used to initialize the operation of the microcontroller 20. Additionally, the patient interface 12 may comprise a memory unit 24 that may comprise a random access memory (RAM) accessible from the microcontroller 20. Further, the memory unit 24 may comprise a shared memory accessible from the microcontroller 20 and the first wireless communication unit 18. The first wireless communication unit 18 may comprise a NFC (near field communication) unit 26, a Bluetooth unit 28 and/or any other wireless communication unit. The NFC unit 26 may comprise a passive NFC component/NFC tag 30 and an NFC antenna 32. The NFC tag 30 is able to store data on the patient interface 12. Alternatively, the NFC unit 26 of the patient interface 12 may also comprise a dual interface NFC unit configured to share data received via a wireless communication with the microcontroller 20 (via the dual interface of the NFC unit).

To the right of a separator 34, shown in FIGS. 2a and 2b, the smartphone 14a and/or the therapy device 14b are arranged, both of which are able to wirelessly communicate with the patient interface 12. The smartphone 14a may comprise a microprocessor 36a. The second wireless communication unit 19a may comprise an NFC unit 38a, a Bluetooth unit 40a and/or any other wireless communication unit. Further, the NFC unit 38a may comprise an active NFC component 42a and an NFC antenna 44a. The active NFC component 42a of the second wireless communication unit 19a is configured to read and/or write data and to actively trigger a wireless communication to a peer entity. In particular, the NFC unit 38a and/or the Bluetooth unit 40a are configured to wirelessly communicate with the respective peer units, namely the NFC unit 26 and/or the Bluetooth unit 28 of the patient interface 12. The wireless communication between the second wireless communication unit 19a of the smartphone 14a and the first wireless communication unit 18 of the patient interface 12 can be established by bringing them into close proximity. The wireless communication can be directly based on a NFC connection or can be based on a Bluetooth connection that is, for example, automatically configured by means of NFC. As a further option, the wireless communication can be realized via a proximity based Bluetooth Low Energy communication.

Additionally, the smartphone 14a may comprise a wireless communication interface 46 configured to establish a wireless communication to a computer system/server 48 that may be located in the Internet 50. The wireless communication of the communication interface 46 may be based on the GSM standard, LTE standard or any other suitable mobile communication standard, like e.g. a Wi-Fi standard.

The therapy device 14b illustrated in FIG. 2b may comprise a similar structure as the smartphone 14a. In particular, the therapy device 14b may comprise a microprocessor 36b. The second wireless communication unit 19b may comprise an NFC unit 38b and/or a Bluetooth unit 40b. The NFC unit 38b may comprise an active NFC component 42b and an NFC antenna 44b. The second wireless communication unit 19b of the therapy device 14b may also wirelessly communicate with the first wireless communication unit 18 of the patient interface 12. The wireless communication can be directly based on a NFC connection or can be based on a Bluetooth connection that is, for example, automatically configured by means of NFC. As a further option, the wireless communication can be realized via a proximity based Bluetooth Low Energy communication.

As illustrated in FIGS. 2a and 2b, the wear-out assessment unit 16 is distributed across the patient interface 12 and the communication device (i.e. the smartphone 14a and the therapy device 14b, respectively). In detail, the wear-out assessment unit 16 comprises a determining component 52, an evaluation component 54 and a presentation component. The determining component 52 is able to determine a wear-out level of the patient interface 12 based on a recorded wear-out of the patient interface 12. By way of example, the wear-out may be recorded/measured by means of a sensor 58 that optionally constitutes a part of the determining component 52. The evaluation component 54 is configured to evaluate the wear-out level and to output a wear-out event if the wear-out level exceeds a predetermined wear-out threshold. The presentation component, for example, is able to acoustically or visually issue a reminder to the patient based on the wear-out event, wherein the reminder is issued to remind the patient to service and/or replace at least parts of the patient interface 12.

In this exemplary embodiment, the determining component 52 and the evaluation component 54 are arranged/implemented on the patient interface 12, whereas the presentation component 56a, 56b is arranged/implemented on the smartphone 14a and the therapy device 14b, respectively. It is to be noted that the components 52, 54, 56 of the wear-out assessment unit 16 can also be distributed in a different way. Some of these options will be described with reference to FIGS. 3 to 5.

Further, the different components 52, 54, 56 of the wear-out assessment unit 16 may be implemented by means of a program code (software) configured to be executed on the microcontroller 20 or the microprocessor 36 or may be realized by means of a hardware component. In the exemplary embodiment illustrated in FIG. 2, the determining component 52, the evaluation component 54 and the presentation component 56a are implemented in software. However, the presentation component 56b of the therapy device 14b is realized as a hardware component, in particular as an LED 56b that might blink to remind the patient to service and/or replace at least parts of the patient interface 12. But also other electronic systems that may be configured to provide a visual and/or audible information can be used to indicate to the patient that at least parts of the patient interface 12 need to be replaced.

In the following, the operation of the wear-out assessment system 10 illustrated in FIG. 2 is explained in detail. When the patient receives a new patient interface 12 from e.g. a mask distributor, the patient touches the patient interface 12 with the smartphone 14a, thereby triggering a wireless communication between the NFC unit 38a of the smartphone 14a and the NFC unit 26 of the patient interface 12. The skilled person acknowledges that it is not necessary to physically contact the patient interface 12 with the smartphone 14a, but is sufficient to bring the smartphone 14a in close proximity to the patient interface 12 to start the NFC communication. If no specific application for handling wear-out data has been installed beforehand on the smartphone 14a, the smartphone 14a contacts a server 48 via the wireless communication interface 46 in order to download a so-called App from an App store that runs on the server 48. The link to the App store may be received via the NFC communication. As an alternative, the App might also be installed on the smartphone 14a by a sleep clinician. After the installation of the App, the smartphone 14a is brought in close proximity to the patient interface 12 to start the NFC communication. On the basis of the NFC communication, the smartphone 14a can retrieve further initial patient interface data (like a serial number, mask type etc.), which have been stored on the patient interface 12, for example right after the manufacturing process, by means of the NFC tag 30.

In this particular embodiment, the App running on the smartphone 14a implements the presentation component 56a of the wear-out assessment unit 16. The presentation component 56a is able to exchange wear-out related data with the evaluation component 54 and the determining component 52 via the Bluetooth units 40a, 28. The Bluetooth communication between the Bluetooth units 40a, 28 is established as soon as the smartphone 14a approaches the patient interface 12. The Bluetooth pairing process can be performed automatically by using credentials that are obtained via reading the NFC tag 30 of the patient interface 12. Also, the information exchange can be performed again by touching the patient interface 12 with the smartphone 14a.

In the currently described embodiment of the wear-out assessment system 10, the determining component 52 comprises a timer for measuring a usage time of the patient interface 12. The timer may be started when the patient receives the patient interface 12 and comes close to the patient interface 12 with the smartphone 14a or the therapy device 14b. The evaluation component 54 continuously monitors the usage time and outputs a wear-out event as soon as the usage time exceeds a predetermined usage time threshold (for example 5.5 months). This wear-out event is communicated to the App/presentation component 56a installed on the smartphone 14a via the Bluetooth units 28, 40a. The presentation component 56a then acoustically or visually issues a reminder to the patient to service and/or replace at least parts of the patient interface 12. Servicing the patient interface 12 might include cleaning a mask sealing flap that forms part of the patient interface 12. As an option, the evaluation component 54 might also consider different thresholds. So, for example, the evaluation component 54 could output a cleaning event every two weeks and could output a replacement event after the expiration of 5.5 months. When issuing the reminder to the patient to replace at least parts of the patient interface 12, the presentation component 56a could in parallel prompt the patient whether some of the parts of the patient interface 12 should be ordered from a mask distributor. If the patient agrees, the confirmed parts of the patient interface 12 are ordered and sent to the patient's home.

The various wear-out events (for example cleaning event, replacement event, etc.) can also be communicated from the evaluation component 54 to the therapy device 14b, for example, by means of the Bluetooth units 28, 40b. As soon as the microprocessor 36b receives the wear-out event, it controls the LED 56b such that the patient is reminded to service and/or replace at least parts of the patient interface 12. In detail, the blinking frequency of the LED 56b may be varied depending on the received wear-out event (cleaning event, replacement event . . . ). Instead of LED 56b, the reminder could also be issued on a user information display of the therapy device 14b.

In another embodiment of the wear-out assessment system 10, the determining component 52 additionally considers output signals of the sensor 58 when measuring the usage time of the patient interface 12. In particular, the sensor 58 may comprise an acceleration sensor that is able to detect a movement of the patient interface 12, thereby detecting a usage of the patient interface 12 and a therapy session respectively. Alternatively or additionally, the sensor 58 may also comprise a contact sensor for detecting a contact between the patient interface 12 and a patient's face. This detection might be based on a measurement of the electric conductivity of the patient's skin. In an example embodiment, the sensor 58 comprises one or more of the following sensor types: a contact sensor for detecting a contact between the patient interface 12 and a patient's face, a pressure sensor for detecting a contact between the patient interface and the patient's face, a temperature sensor for detecting a temperature of a skin contact surface of the patient interface; a humidity sensor for detecting an amount of moisture in an area between the patient interface and the patient's face, and an elongation sensor for detecting an elongation within a headgear of the patient interface.

In case the sensor 58 comprises at least the acceleration sensor, the usage of the patient interface 12 is detected due to the general movement of the patient interface 12 during a therapy session. Moreover, the usage of the patient interface 12 may also be detected by a characteristic moving pattern of the patient interface 12 during the treatment. As a result of these additionally provided sensor signals, the timer of the determining component 52 is able to measure only the time when the patient actually uses the patient interface 12 for the medical treatment. As described above, the evaluation component 54 evaluates this usage time by comparing the measured usage time with a predetermined wear-out threshold or a plurality of predetermined thresholds. As soon as the usage time exceeds one of the thresholds, the evaluation component 54 outputs a respective wear-out event. This event is forwarded to the presentation components 56a, 56b of the smartphone 14a and therapy device 14b, respectively.

In a further embodiment of the wear-out assessment system 10, the sensor 58 may comprise a pressure sensor configured to monitor the pressure of the patient interface 12 during the pressure therapy. The determining component 52 and the evaluation component 54 might then collect pressure data that are related to the output signals of the integrated pressure sensor. These pressure data can then be provided to the smartphone 14a/therapy device 14b by means of the Bluetooth units 28, 40a/40b.

Figure 3:
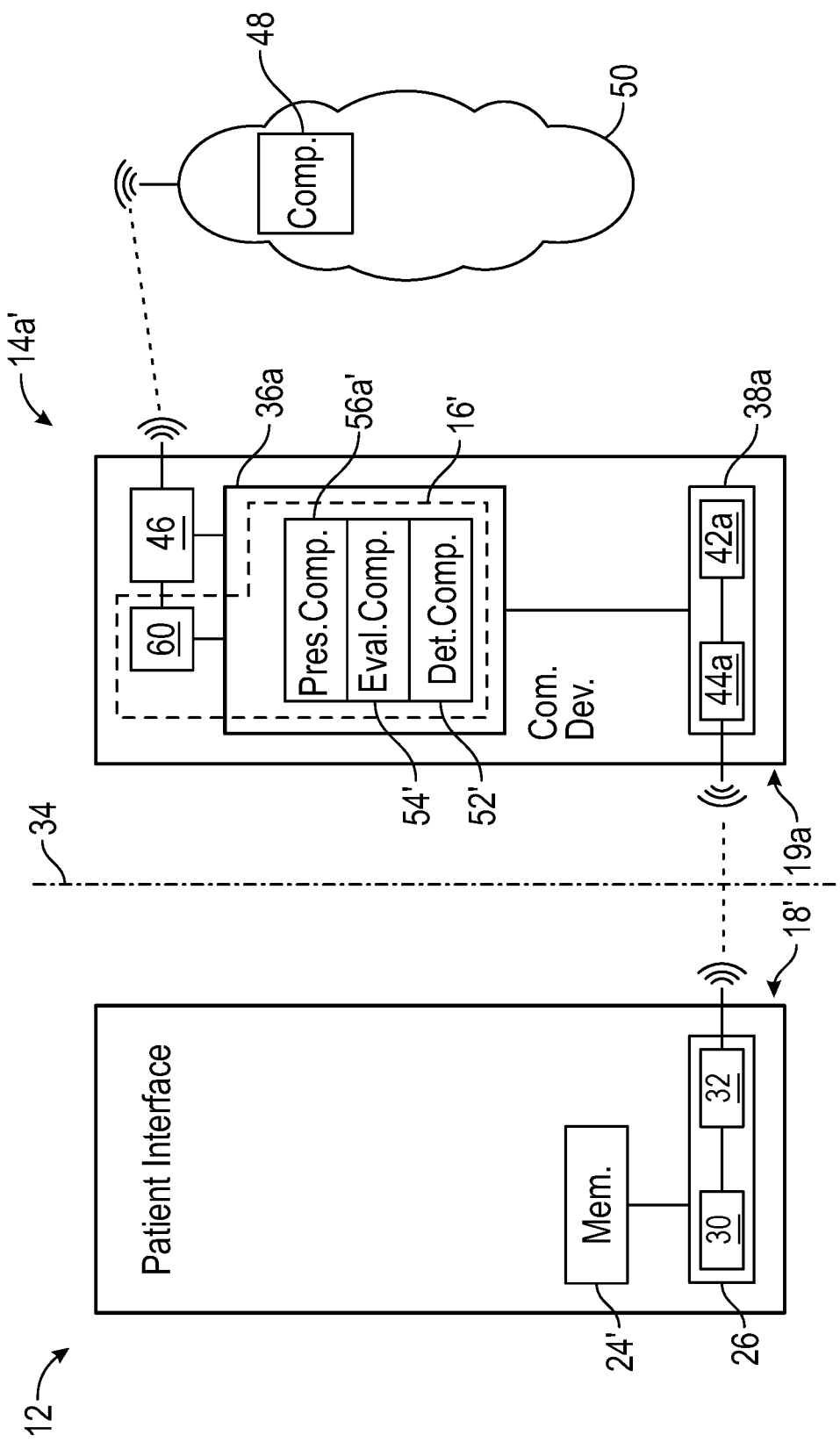
FIGS. 3 to 5 show further detailed embodiments of the proposed wear-out assessment system and the proposed patient interface.
Figure 4A:
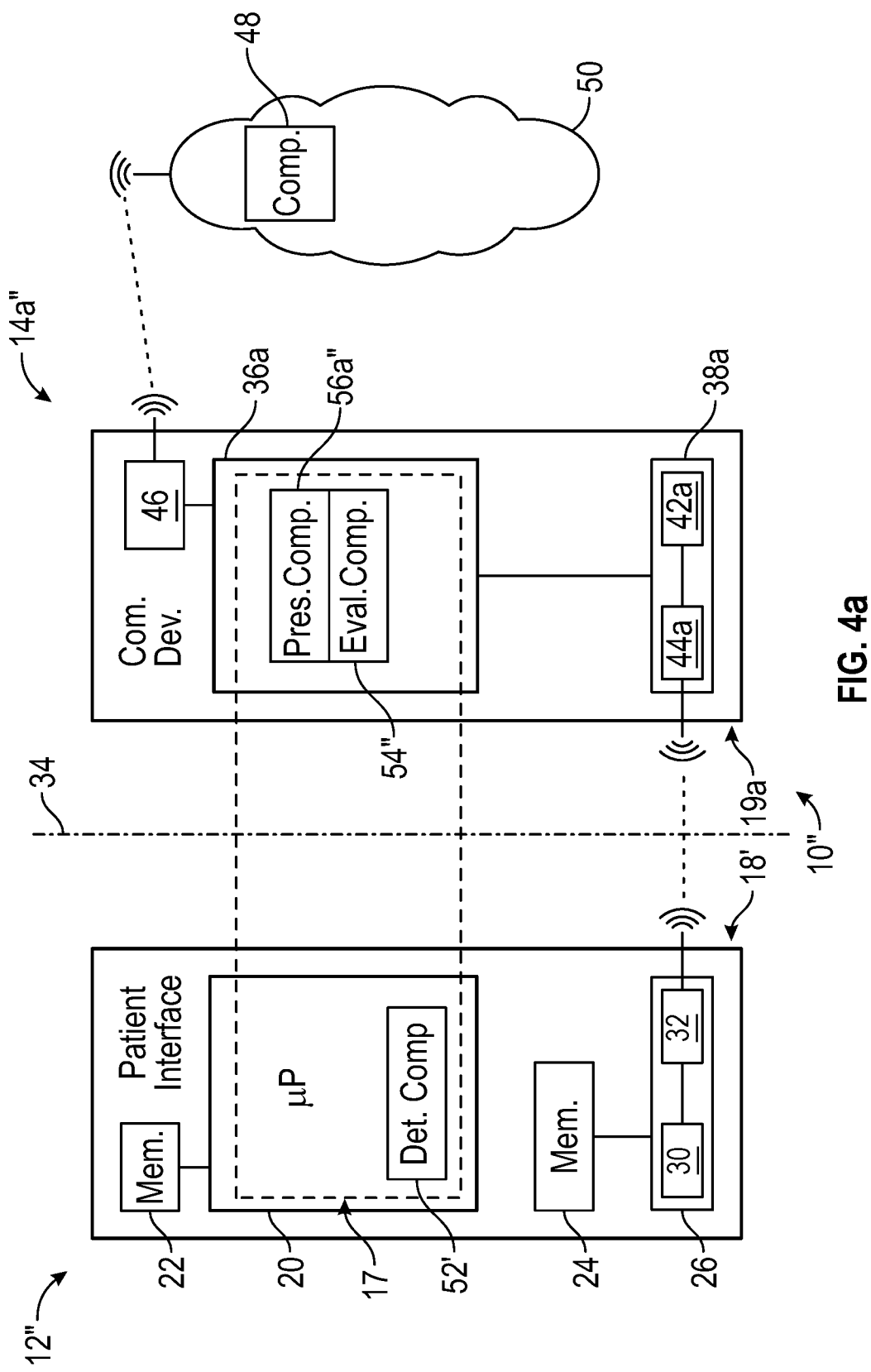
Figure 4B:
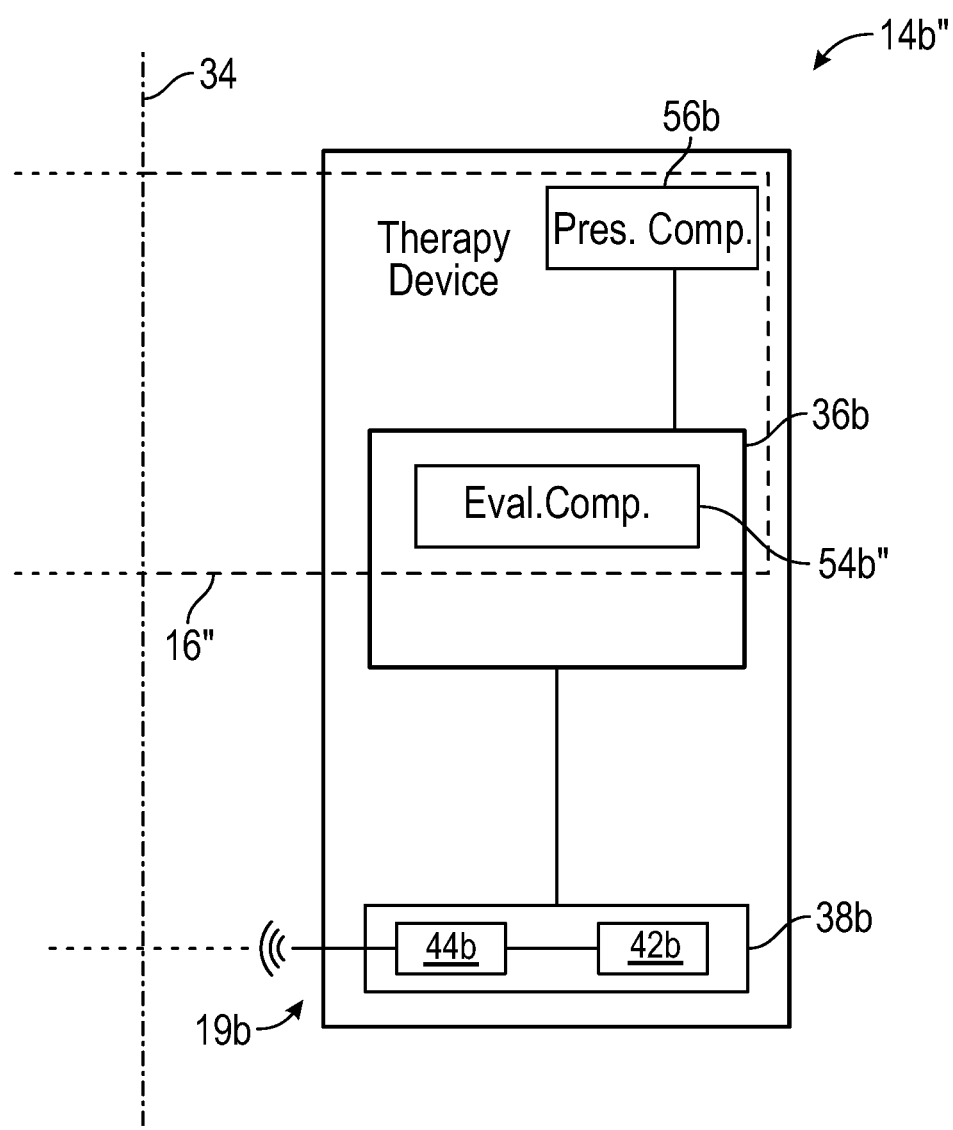
Figure 5:
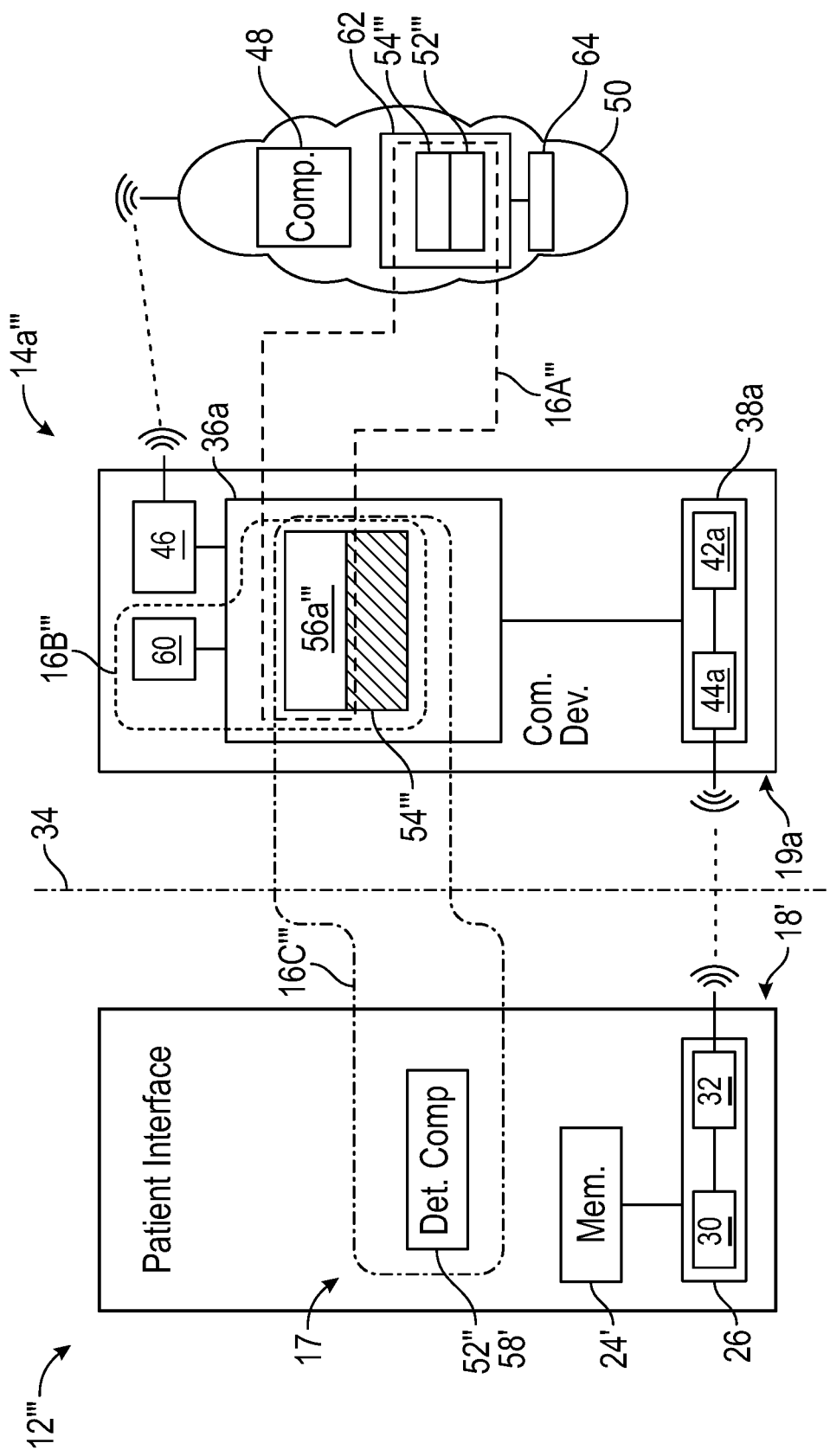

FIGS. 3 to 5 illustrate further embodiments of the wear-out assessment system 10 and the patient interface 12. These embodiments are similar to the wear-out assessment system 10 and the patient interface 12 illustrated in FIG. 2 in regard to the general structure and functionality. Thus, same elements are denominated with the same reference signs. In the following, only the differences will be described.

As far as the embodiment of FIG. 3 is concerned, the patient interface 12' only comprises the (dual interface) memory unit 24' and a first wireless communication unit 18' which comprises the NFC unit 26. In this embodiment, the memory unit 24' is configured to store initial patient interface data of the patient interface 12', even if unpowered. The smartphone 14a' illustrated in FIG. 3 does not comprise the Bluetooth unit 40a. It is to be noted, however, that the patient interface 12' and the smartphone 14a' may comprise the same components as the patient interface 12 and the smartphone 14a of FIG. 2. In FIG. 3, only those components are shown which are necessary to provide the described functionality of the wear-out assessment system 10'.

As can be seen from FIG. 3, the wear-out assessment unit 16' comprises the determining component 52', the evaluation component 54' and the presentation component 56a', wherein all of these components are implemented as a program code (App) that is able to be executed on the microprocessor 36a. In this exemplary embodiment, the determining component 52' may comprise a counter for measuring a usage count of the patient interface 12'. The evaluation component 54' compares the usage count with a predetermined usage count threshold. As soon as the usage count exceeds the predetermined usage count threshold, the evaluation component 54' outputs a wear-out event. When the presentation component 56a' receives the wear-out event, it may issue a reminder to the patient to service and/or replace at least parts of the patient interface 12'.

In this embodiment, the usage counter of the determining component 52' is increased each time an approach between the patient interface 12' and the smartphone 14a' is detected by means of the NFC unit 38a. So, the patient is required to touch the patient interface 12' with the smartphone 14a' for each therapy session. As soon as the distance between the smartphone 14a' and the patient interface 12' falls below a predetermined threshold, the NFC unit 38a wirelessly communicates with the NFC unit 26, thereby retrieving the initial patient interface data stored on the patient interface 12'. On the basis of the initial patient interface data, the patient interface 12' can be identified as the patient interface owned by the patient. Thus, it might be possible to only increase the usage counter if the smartphone 14a' approaches the own patient interface 12'.

When the reminder is issued to the patient to replace at least parts of the patient interface 12', the presentation component 56a' can in parallel query the patient whether these parts of the patient interface 12' should be automatically ordered from a mask distributor. If the patient agrees, these parts will be ordered and sent to the patient's home.

Optionally, the determining component 52' can additionally comprise a timer for measuring the usage time of the patient interface 12'. The evaluation component 54' then takes into account the measured usage time and usage count when evaluating the wear-out level of the patient interface 12'.

Moreover, the determining component 52' may additionally comprise a camera 60. When the evaluation component 54' determines that the usage time and/or usage count have reached the respective predetermined thresholds, the evaluation component 54' outputs a camera event, which triggers the presentation component 56a' to issue a reminder to the patient to take a photo of the patient interface 12', in particular of a mask sealing flap of the patient interface 12'. As soon as the patient has captured this photo by means of the camera 60, the evaluation component 54' starts an analysis of the captured photo. If the patient has not cleaned the patient interface 12' for a long time, there will be, for example, a large biofilm on the mask sealing flap of the patient interface 12'. This biofilm may cause the color and/or transparency of the mask sealing flap to change, e.g. the mask sealing flap may become more opaque or yellow. For a better reference, the evaluation component 54' may compare the characteristics of this captured photo with the characteristics of an initial photo of the mask sealing flap that has been taken during the manufacturing process. The characteristics of the initial photo may have been stored, for example, on the memory 24'. In order to retrieve the characteristics of the initial photo, the smartphone 14a' is brought into close proximity to the patient interface 12', thereby triggering an NFC communication between the NFC units 38a, 26. If the evaluation component 54' comes to the result that the transparency of the mask sealing flap has degraded under a predetermined level, it outputs a cleaning event to the presentation component 56a', which issues a reminder to the patient to clean the patient interface 12'. After the cleaning event, the evaluation component 54' may issue another camera event in order to ask the patient to take another photo of the cleaned mask sealing flap. Afterwards, the evaluation component 54' again compares the characteristics of the photo of the cleaned patient interface 12' with the characteristics of the initial photo. If the color and/or transparency of the mask sealing flap remains unchanged due to a strong biofilm formation, the evaluation component 54' outputs a replacement event to the presentation component 56a' which, in turn, issues a reminder to the patient to replace the mask sealing flap of the patient interface 12'. In parallel, the presentation component 56a' can prompt the patient whether the mask sealing flap should be automatically ordered from a mask distributor. After the confirmation of the patient, the mask sealing flap is ordered and it sent to the patient's home.

FIG. 4 shows another embodiment of the wear-out assessment system 10". The patient interface 12" comprises an architecture that is similar to that of patient interface 12, besides the missing communication (Bluetooth) unit 28. However, it goes without saying that the patient interface 12" may also comprise the Bluetooth unit 28 without restricting the functionality of the wear-out assessment system 10". This analogously applies to the smartphone 14*a*" and the therapy device 14*b*". As illustrated in FIG. 4, the wear-out assessment unit 16" comprises the determining component 52", the evaluation component 54*a*", 54*b*", and the presentation component 56*a*", 56*b*. The determining component 52" is arranged on the patient interface 12", whereas the evaluation component 54*a*", 54*b*" and the presentation component 56*a*", 56*b* are arranged on the smartphone 14*a*" and the therapy device 14*b*", respectively.

In the present embodiment, the determining component 52" comprises a counter for measuring a usage count of the patient interface 12". For each therapy session, for example every night when the patient uses the patient interface 12", the patient comes close to the NFC unit 38*b* of the therapy device 14*b*" with the patient interface 12". To enforce this procedure, the wireless connection between the therapy device 14*b*" and the patient interface 12" could play a role in the activation of the therapy device 14*b*". In particular, coming close the therapy device 14*b*" with the patient interface 12" could unlock the general operation of the therapy device 14*b*" in that pressurized air is only delivered to the patient interface 12" after the therapy device 14*b*" has been unlocked by means of the patient interface 12".

As soon as the patient interface 12" approaches the therapy device 14*b*" a wireless communication between the NFC units 26 and 38*b* is started. The NFC unit 38*b* comprises the active NFC component 42*b* and accordingly is able to actively read and write data over the wireless communication. When an approach between the patient interface 12" and the therapy device 14*b*" is detected by means of the NFC units 26, 38*a*, the determining component 52" increases the usage count of the patient interface 12". Further, the active NFC component 42*b* reads the updated usage count and forwards this information to the evaluation component 54*b*". The evaluation component 54*b*" evaluates the usage count and outputs a wear-out event if the usage count exceeds a predetermined usage count threshold. As a result of the wear-out event, the microprocessor 36*b* controls the LED 56*b* such that it starts blinking to indicate to the patient that at least parts of the patient interface 12" need to be replaced. Instead of LED 56*b*, other electronic systems such as sound, voice information systems can be used to indicate to the patient that at least parts of the patient interface 12" need to be replaced. The patient can then manually order the respective parts of the patient interface 12". Alternatively, the patient brings the smartphone 14*a*" in close proximity to the patient interface 12" to start an App and collect the patient interface parameters via an NFC communication. The evaluation component 54*a*" can then retrieve the usage counter from the determining component 52". If the usage count exceeds the predetermined usage count threshold, the evaluation component 54*a*" outputs the wear-out event to the presentation component 56*a*". The presentation component 56*a*", in turn, prompts the patient whether the respective parts of patient interface 12" should be ordered from the mask distributor.

It is to be noted that the patient interface 12" could also comprise the general structure of the patient interface 12', illustrated in FIG. 3. In such an embodiment, the active NFC component 42*b* of the therapy device 14*b*" reads the actual usage count of the patient interface 12" stored on the memory 24', increases the usage count by one and writes the updated usage count back to the memory 24'. Consequently, this embodiment can provide the same functionality as the embodiment described with reference to FIG. 4.

By storing the usage data (e.g. the usage count) in the NFC tag 30/memory unit 24', multiple patient interfaces can be used without the need to keep track of the individual patient interfaces in the therapy device 14*b*". Additionally, the NFC enabled smartphone 14*a*" can be used to check on the usage data of each patient interface at any time.

The initial patient interface data (like e.g. serial number, type of mask, expected mask duration . . . ) can be stored on the NFC tag 30/memory 24' during a factory configuration or can be optionally configured by a mask supply center.

FIG. 5 shows a further embodiment of the wear-out assessment system 10'''. The structure of the patient interface 12''' is similar to the patient interface 12' illustrated in FIG. 3. However, patient interface 12''' additionally comprises the sensor 58', which forms part of the determining component 52'''. According to the embodiment illustrated in FIG. 5, a second computer system/server 62 is located in the Internet 50 that has access to a database 64. Further, FIG. 5 illustrates three different embodiments of the wear-out assessment unit, namely the wear-out assessment units 16A''', 16B''', 16C''', which can be combined with each other during an operation flow of the wear-out assessment system 10'''. The second server 62 is configured to run at least parts of the wear-out assessment unit 16A'''.

In this embodiment, the initial patient interface data (like serial number, mask type, mask identification, expected mask duration . . . ) are stored on the NFC tag 30/memory 24' during the manufacturing process. Optionally, the initial patient interface data can also be configured on the patient interface 12''' by a mask supply center. When the patient interface 12''' is activated during the first use (e.g. by coming close the patient interface 12''' with the NFC enabled smartphone 14*a*'''), the smartphone 14*a*''' retrieves at least parts of the initial patient interface data, identifies the specific patient interface 12''' based on these data and downloads a mask App compatible to patient interface 12''' from an App store running on the server 48 to the smartphone 14*a*'''. In parallel, the smartphone 14*a*''' forwards at least parts of the initial patient interface data to a cloud service running on the second server 62. The cloud service comprises the determining component 52''' and the evaluation component 54'''. The determining component 52''', in turn, comprises a timer for measuring a usage time of the patient interface 12'''. When the determining component 52''' receives the initial patient interface data, it associates these data with a respective patient profile stored in the database 64 and starts the timer associated with the patient interface 12'''. By means of this concept, the cloud service is able to manage the wear-out of a plurality of patient interfaces. The evaluation component 54''' checks whether the measured usage time exceeds a predetermined usage time threshold (for example 5.5 months). If the usage time exceeds the threshold, the evaluation component 54''' sends a wear-out event to the presentation component 56*a*''' running on the smartphone 14*a*'''. If the wear-out event comprises a cleaning event, the presentation component 56*a*''' issues an alert to the patient that the patient interface 12''' should be cleaned. In case the wear-out event comprises a replacement event, the presentation component 56a''' queries the patient whether parts of the patient interface 12''' should be ordered from a mask distributor. Optionally, the evaluation component 54''' may also output a camera event. The presentation component 56a''' will then ask the patient to take a photo of the patient interface 12''' by means of the camera 60. In particular, the patient may be asked to take a photo of a mask sealing flap of the patient interface 12'''. The captured photo will then be evaluated by the evaluation component 54''' running on the smartphone 14a''' as described before with reference to FIG. 3. When evaluating a photo taken by the camera 60, a wear-out assessment unit 16B''' is dynamically formed, which comprises the camera 60 (as the determining component 52'''), the evaluation component 54''' running on the smartphone 14a''' and the presentation component 56a'''.

As a further option, the evaluation component 54''' running on the second server 62 may output a re-check event, which triggers the patient (by means of the presentation component 56a''') to re-check the actual wear-out of the patient interface 12''' by touching the patient interface 12''' with the smartphone 14a'''. Particularly, the sensor 58' of the patient interface 12''' may comprise any sensor that is suitable for measuring the wear-out of the patient interface 12'''. Examples of such sensors are flow sensors determining increased leakage due to a degradation of the silicone flap, or force sensors determining higher strapping forces of the mask to be applied by the patient because of increased leakage due to a degradation of the silicone flap or the straps. Other sensors could be motion sensors such as accelerometers determining high motion of the patient during sleep caused by leakage of the mask created by degradation of the silicone flap or the straps. Other examples of sensors for wear out are color sensors that detect changes of color due to biofilm formation or stained biofilms on the flap. It goes without saying that the sensors are not restricted to these exemplary sensors. Other sensors could be a temperature sensor for measuring a temperature of the patient's face, a humidity sensor for measuring an amount of moisture in a sealed area between the patient's face and the patient interface, or a humidity sensor for determining an elongation within a headgear oft eh patient interface.

The sensors 58' can then be read via energy harvesting by the NFC tag 30 which is configured to power electronics in the patient interface 12''' and thereby enables a one time readout of the sensor 58'. In detail, the wear-out information provided by the sensor 58' is retrieved from the evaluation component 54''' of the smartphone 14a''' via the NFC units 38a, 26. The evaluation component 54''' of the smartphone 14a''' again evaluates the retrieved wear-out information and outputs respective events to the presentation component 56a''' if the provided wear-out information exceeds a predetermined wear-out level. By re-checking the wear-out of the patient interface 12''', a wear-out assessment unit 16C''' is dynamically formed, which comprises the sensor 58' (as the determining component 52'''), the evaluation component 54''' running on the smartphone 14a''' and the presentation component 56a'''.

Figure 6:
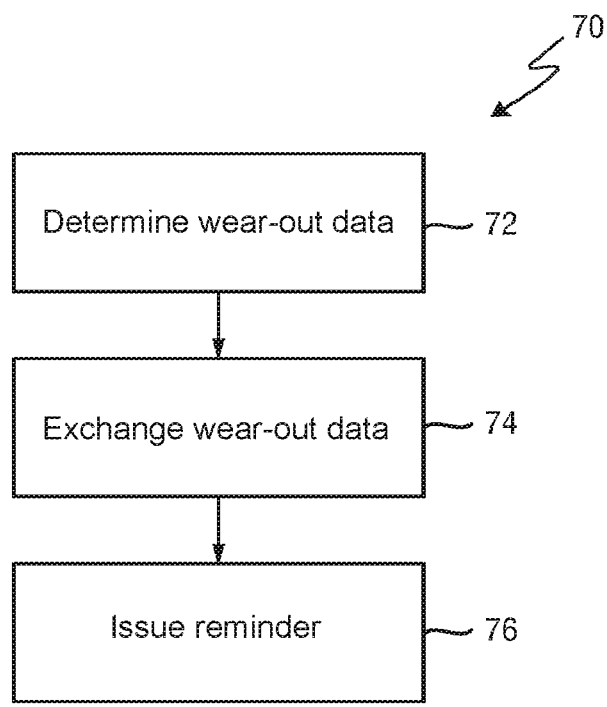
FIG. 6 shows a flow diagram illustrating the proposed method for assessing the wear-out of the patient interface.

FIG. 6 shows a flow diagram illustrating a method 70 for assessing the wear-out of the patient interface 12. As an example, a computer program product such as the App running on the smartphone 14a' illustrated in FIG. 3 may comprise code for causing the microprocessor 36a, when the code is executed on the microprocessor 36a, to enable the wear-out assessment system 16' to execute the method 70. In a first step 72, wear-out data relating to the wear-out of the patient interface 12 are determined. The wear-out data may comprise output signals from the sensor 58, pictures from the camera 60, the usage time, the usage count, initial patient interface data (e.g. serial number, type of mask, expected mask duration an QR-code etc.) and/or several different wear-out events (cleaning event, replacement event, camera event, re-check event etc.). It goes without saying that the wear-out data are not restricted to these exemplary data. In a next step 74, at least parts of these wear-out data are exchanged between the patient interface 12 and the communication device by means of a wireless communication between the respective first and second wireless communication units 18, 19. In a further step 76, a reminder is issued on the communication device to remind the patient to service and/or replace at least parts of the patient interface 12, wherein the reminder is issued in dependence of the previously determined wear-out data.

Figure 7:
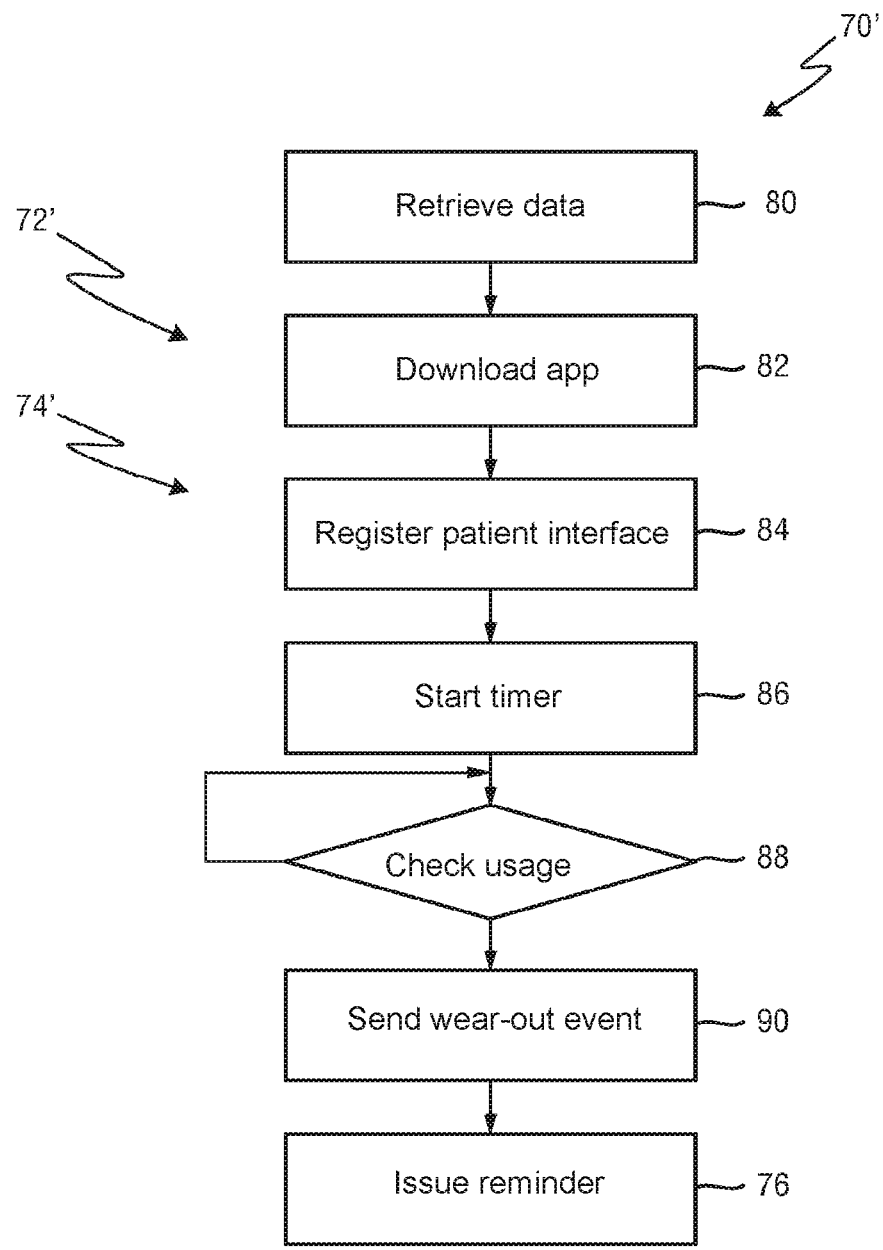
FIG. 7 shows another embodiment of the proposed method.

FIG. 7 shows another embodiment of the method 70'. The steps 72', 74' of determining and exchanging the wear-out data comprise steps 80 through 90, which are now described in more detail with respect to the embodiment of the wear-out assessment system 10''' illustrated in FIG. 5. In step 80, initial patient interface data are retrieved by the smartphone 14a''' from the patient interface 12''' via a wireless communication between the NFC units 38a, 26. As an example, the initial patient interface data may comprise a link to an App store running on the server 48. In step 82, a computer program (i.e. the App) matching the patient interface 12''' is downloaded to the smartphone 14a''' from the App store. As soon as the App is downloaded and installed on the smartphone 14a''', further initial patient interface data are retrieved by the smartphone 14a''' from the patient interface 12''' via a wireless communication between the NFC units 38a, 26, wherein the wireless communication is established by again touching the patient interface 12''' with the smartphone 14a'''. The App then sends at least parts of the initial patient interface data to a cloud service running on the second server 62, thereby registering the patient interface 12''' at the cloud service (step 84). Upon receipt of the initial patient interface data, the cloud service starts a timer for measuring the usage time of the patient interface 12''' (step 86). In step 88, the evaluation component 54''' of the cloud service checks whether the measured usage time exceeds a predetermined usage time threshold. This threshold can be for example 5.5 months, but can be also any other suitable time interval. As soon as the cloud service determines that the measured usage time exceeds the predetermined threshold, it sends a wear-out event to the App, in particular to the presentation component 56a''', running on the smartphone 14a''' (step 90). Depending on the specific wear-out event, the presentation component 56a''' issues in step 76 a reminder to the patient to service and/or replace at least parts of the patient interface 12'''.

In an alternative embodiment, the cloud service can also be used to monitor a usage count, output signals of wear-out sensors (arranged e.g. on the patient interface 12''') and/or other data suitable for evaluating the wear-out of the patient interface 12'''.

Figure 8:
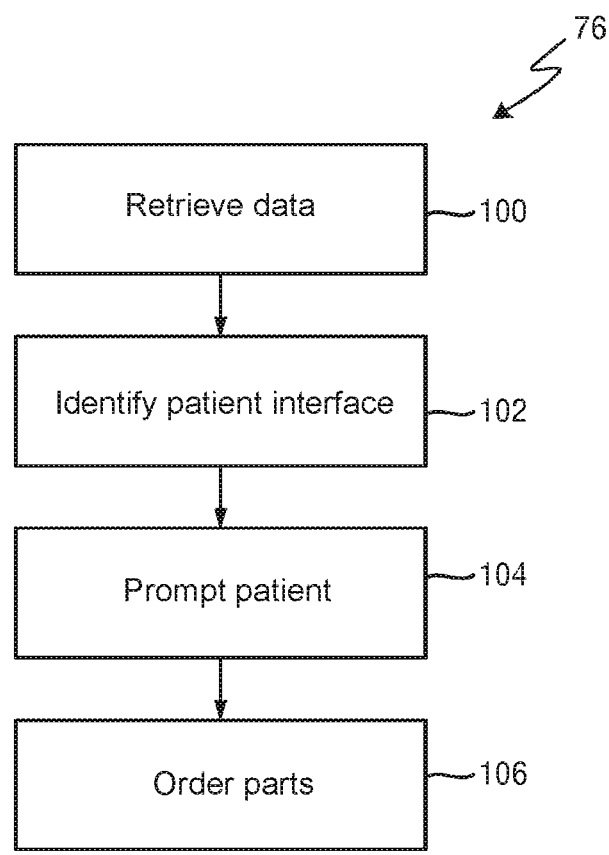
FIGS. 8 and 9 show flow diagrams illustrating further details of the proposed method as described with reference to FIGS. 6 and 7.

FIG. 8 shows a flow diagram illustrating further details of step 76, namely the issuance of the reminder. In a step 100, initial patient interface data stored on the patient interface 12 are retrieved. In a further step 102 the patient interface 12 is identified by means of the initial patient interface data. In a next step 104, the patient is prompted whether at least parts of the patient interface (for example a mask sealing flap) should be ordered from a mask distributor. If the patient agrees, the respective parts of the patient interface 12 are ordered in a step 106. This automatic ordering process makes it very comfortable for the patient to organize new replacement parts of the patient interface 12.

Figure 9:
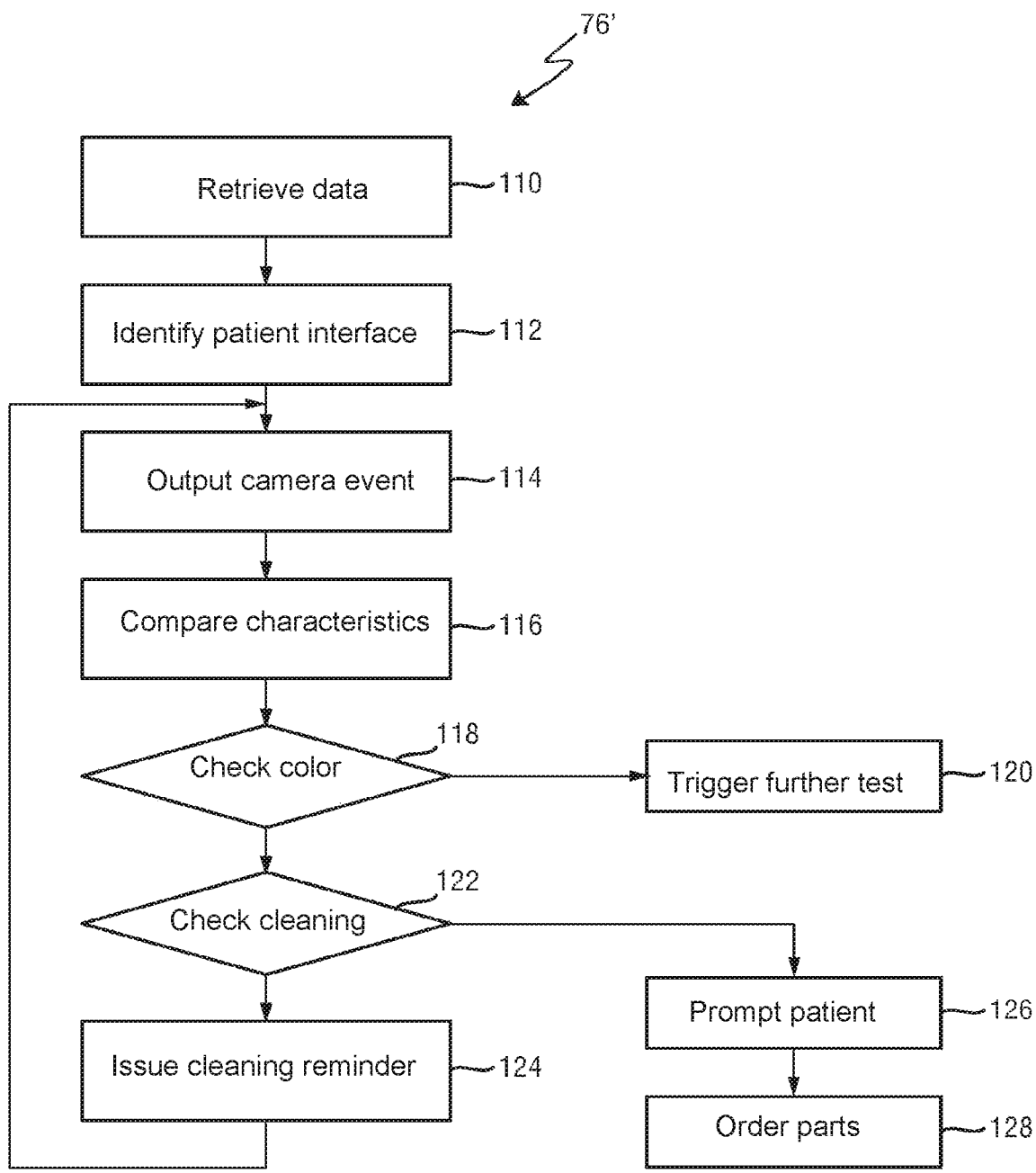

FIG. 9 illustrates another embodiment of step 76', which will now be explained with reference to the embodiment of the wear-out assessment system 10' illustrated in FIG. 3. In particular in a step 110, the evaluation component 54' retrieves initial patient interface data via the NFC units 26, 38a from the patient interface 12'. The initial patient interface data including characteristics of an initial photo of a mask sealing flap of the patient interface 12' have been stored in the NFC tag 30/memory 24' during the manufacturing process. In a step 112, the evaluation component 54' running on the smartphone 14a' identifies the patient interface 12' by means of the initial patient interface data. In step 114, the evaluation component 54' outputs a camera event to the presentation component 56a', which issues a reminder to the patient to take a photo of the mask sealing flap. As soon as this picture has been taken by means of the camera 60, the evaluation component 54' compares the characteristics of the new photo with the characteristics of the initial photo of the mask sealing flap (step 116). If the patient interface 12' has not been cleaned for a certain period of time, a biofilm has grown on the mask sealing flap. As a result, the color and/or transparency of the mask sealing flap may change, e.g. the mask sealing flap may become more opaque or yellow. Accordingly, the color and/or transparency of the mask sealing flap is checked by the evaluation component 54' in a step 118. If it is determined in step 118 that the color and/or transparency of the mask sealing flap is still acceptable, further tests/checks may be triggered in a step 120. However, if a changed color and/or degraded transparency of the mask sealing flap is determined in step 118, it is checked in a step 122 whether a cleaning event has already output from the evaluation component 54'. If not, such a cleaning event is output and the patient is asked to clean the mask sealing flap (by issuing a reminder via the presentation component 56a'). After the cleaning of the patient interface 12' has been confirmed by the patient, the method goes back to step 114 and asks the patient to again take a picture of the cleaned mask sealing flap. Then, the evaluation component 54' compares the characteristics of the newest picture with the characteristics of the initial picture of the mask sealing flap in step 116. If the color and/or transparency of the mask sealing flap has remained (step 118), the patient is prompted in a step 126 whether at least parts of the patient interface 12', in particular the mask sealing flap, should be ordered from a mask distributor. If the patient agrees, the confirmed parts of the patient interface 12' will be ordered automatically (step 128).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A wear-out assessment system comprising:
    a patient interface for delivering a flow of breathable gas to an airway of a patient, wherein the patient interface comprises a first wireless communication unit,
    a communication device comprising a second wireless communication unit configured to wirelessly communicate with the first wireless communication unit, and
    a wear-out assessment unit including,
        a determining component including a sensor for detecting usage of the patient interface for medical treatment and a timer for measuring a usage time of the patient interface device for medical treatment, the determining component being configured to determine a wear-out level of the patient interface based on the usage time of the patient interface for medical treatment,
        an evaluation component for evaluating the wear-out level and for outputting a wear-out event if the wear-out level exceeds a predetermined wear-out threshold, and
        a presentation component for issuing a reminder to the patient based on the wear-out-event,
    wherein the determining component is configured to trigger the timer to measure the usage time of the patient interface for medical treatment in response to the sensor detecting usage of the patient interface for medical treatment,
    wherein the wear-out assessment unit is distributed between the patient interface and the communication device with at least the determining component being on the patient interface device and at least the presentation component being on the communication device, and
    wherein the first and second wireless communication units are structured to exchange at least one of the wear-out level and the wear-out event.

2. The wear-out assessment system according to claim 1, wherein the sensor comprises a motion sensor for measuring a movement of the patient interface.

3. The wear-out assessment system according to claim 1, wherein the sensor comprises one or more of the following:
    a contact sensor for detecting a contact between the patient interface and a patient's face,
    a pressure sensor for detecting a contact pressure between the patient interface and the patient's face,
    a temperature sensor for detecting a temperature of a skin contact surface of the patient interface;
    a humidity sensor for detecting an amount of moisture in an area between the patient interface and the patient's face;
    an elongation sensor for detecting an elongation within a headgear of the patient interface.

4. The wear-out assessment system according to claim 1, wherein the wear-out assessment unit comprises a camera for capturing an image of the patient interface, and wherein the evaluation components is configured to compare properties of the captured image to a reference image.

5. The wear-out assessment system according to claim 1, wherein the communication device is a mobile communication device or a therapy device for providing pressurized air to the patient interface.

6. The wear-out assessment system according to claim 5, wherein the therapy device is configured to be activated if an approach between the patient interface and the therapy device is detected by means of the second wireless communication unit.

7. A patient interface for delivering a flow of breathable gas to an airway of a patient, comprising:
- a wireless communication unit for wirelessly communicating with a communication device, and
- a wear-out assessment module including;
  - a determining component including a sensor for detecting usage of the patient interface for medical treatment and a timer for measuring a usage time of the patient interface device for medical treatment, the determining component being configured to determine a wear-out level of the patient interface based on the usage time of the patient interface for medical treatment, and
  - an evaluation component for evaluating the wear-out level and for outputting a wear-out event if the wear-out level exceeds a predetermined wear-out threshold,
- wherein the determining component is configured to trigger the timer to measure the usage time of the patient interface for medical treatment in response to the sensor detecting usage of the patient interface for medical treatment, and
- wherein the wireless communication unit is structured to wirelessly communicate the wear-out event to the communication device.

8. A method for assessing a wear-out of a patient interface configured to deliver a flow of breathable gas to an airway of a patient, the method comprising:
- determining, with a determining component on the patient interface and including a sensor for detecting usage of the patient interface for medical treatment and a timer for measuring a usage time of the patient interface device for medical treatment, a wear-out level of the patient interface based on the usage time of the patient interface for medical treatment,
- evaluating, with an evaluation component on the patient interface, the wear-out level and outputting a wear-out event if the wear-out level exceeds a predetermined wear-out threshold,
- communicating the wear-out event from the patient interface to a communication device by wireless communication and
- issuing, on the communication device, a reminder to the patient to service and/or replace at least parts of the patient interface based on the wear-out event.

9. The method according to claim 8, wherein issuing the reminder comprises:
- retrieving initial patient interface data stored on the patient interface,
- identifying the patient interface based on the initial patient interface data,
- prompting the patient whether at least parts of the patient interface should be ordered from a mask distributor, and
- ordering the parts of the patient interface in response to an order of the patient.

10. A non-transitory computer readable medium comprising a computer program for causing a computer to carry out a method for assessing a wear-out of a patient interface configured to deliver a flow of breathable gas to an airway of a patient when said computer program is carried out on the computer, the method comprising:
- determining, with a determining component on the patient interface and including a sensor for detecting usage of the patient interface for medical treatment and a timer for measuring a usage time of the patient interface device for medical treatment, a wear-out level of the patient interface based on the usage time of the patient interface for medical treatment,
- evaluating, with an evaluation component on the patient interface, the wear-out level and outputting a wear-out event if the wear-out level exceeds a predetermined wear-out threshold,
- communicating the wear-out event from the patient interface to a communication device by wireless communication and
- issuing, on the communication device, a reminder to the patient to service and/or replace at least parts of the patient interface based on the wear-out event.

* * * * *